(12) United States Patent
Cotoras et al.

(10) Patent No.: US 7,951,578 B2
(45) Date of Patent: May 31, 2011

(54) BACTERIAL STRAIN FOR A METAL BIOSORPTION PROCESS

(75) Inventors: Davor Cotoras, Santiago (CL); Pabla Viedma, Santiago (CL)

(73) Assignees: Universidad de Chile, Santiago (CL); Biotechnologies del Agua Ltda., Santiago (CL)

( * ) Notice: Subject to any disclaimer, the term of this patent is extended or adjusted under 35 U.S.C. 154(b) by 899 days.

(21) Appl. No.: 11/819,211

(22) Filed: Jun. 26, 2007

(65) Prior Publication Data
US 2008/0009054 A1 Jan. 10, 2008

(30) Foreign Application Priority Data
Jul. 4, 2006 (CL) .................................. 1737-2006

(51) Int. Cl.
*C12N 1/20* (2006.01)
(52) U.S. Cl. .................................. 435/252.5; 424/93.4
(58) Field of Classification Search .................. None
See application file for complete search history.

(56) References Cited

U.S. PATENT DOCUMENTS

| | | | |
|---|---|---|---|
| 4,769,223 A | 9/1988 | Volesky et al. |
| 4,898,827 A | 2/1990 | Brierley et al. |
| 5,005,130 A | 4/1991 | Breen et al. |
| 5,055,402 A | 10/1991 | Greene et al. |
| 5,279,745 A | 1/1994 | Jeffers et al. |
| 5,422,268 A | 6/1995 | Rusin |
| 5,538,645 A | 7/1996 | Yannai et al. |
| 5,602,071 A | 2/1997 | Summers, Jr. et al. |
| 5,648,313 A | 7/1997 | Pohl |
| 5,789,204 A | 8/1998 | Kogtev et al. |
| 5,976,847 A | 11/1999 | Hermann |
| 2006/0070949 A1 | 4/2006 | Tadic et al. |

FOREIGN PATENT DOCUMENTS
CA 2497264 3/2004

OTHER PUBLICATIONS

Lo et al..(Appl Biochem Biotechnol. 2003 Spring;105-108:581-91.*
Leung et al..( Biosorption of heavy metals by bacteria isolated from activated sludge. Leung WC, Chua H, Lo W. Appl Biochem Biotechnol. 2001 Spring;91-93:171-84.*
He et al..("Surface charge properties of and Cu(II) adsorption by spores of the marine *Bacillus* sp. strain SG-1," American Chemical Society National Meeting, 213:176 , 1997. ).*
Philip et al..(International Journal of Environment and Pollution 2001—vol. 15, No. 4 pp. 448-460).*
Nourbakhsh et al., Chemical Engineering Journal 85 (2002) 351-355.*
Bregni et al., Ars Pharmaceutica, 41:3; 245-248, 2000).*
Gadd et al., Microbial Treatment of Metal Pollution—A Working Biotechnology?, Trends Biotechnol, vol. 11, pp. 353-359, dated 1993.
Fourest et al., Heavy metal biosorption by fungal mycelial by-products: mechanism and influence of pH., Appl. Microbiol. Biotechnol, vol. 37, pp. 399-403, dated 1992.
Kapoor et al., Fungal Biosorption—An Alternative Treatment Option for Heavy Meal Bearing Wastewaters: A Review. Bioresource Technology, vol. 53, pp. 195-206, dated 1995.
Kratochvil et al., Advances in the biosorption of heavy metals, Trends Biotechnol., vol. 16, pp. 291-300, dated 1998.
Volesky et al., Biosorption of heavy metals, Biotechnol. Prog., vol. 11, pp. 235-250, dated 1995.
Volesky, Detoxification of metal-bearing effluents: biosorption for the next century, Hydrometallurgy, vol. 59, pp. 203-216, dated 2001.
Brierley, Production and application of a Bacillus-based product for use in metals biosorption. In: B. Volesky, Editor, Biosorption of Heavy Metals, CRC Press, Boca Raton, FL, pp. 305-311, dated 1990.
Brierley et al., Immobilization of biomass for industrial application of biosorption. In: A.E. Torma, M.L. Apel and C.L. Brierley, Editors, Biohydrometallurgical Technologies, Proceedings of the International Biohydrometallurgy Symposium, The Minerals, Metals and Materials Society, Warrendale, PA, pp. 35-44, dated 1993.
Castro et al., Biomasa de Rhizopus oligosporus como adsorbente de iones metalicos. Microbiologia Sem, vol. 8, pp. 94-105, dated 1992.
Cotoras et al., Biosorption of metal ions by Azotobacter vinelandii, World Journal of Applied Microbiology and Biotechnology, vol. 8, pp. 319-323, dated 1992.
Cotoras et al., Sorption of metal ions by whole cells of Bacillus and Micrococcus Environmental Technology, vol. 13, pp. 551-559, dated 1992.
Holan et al., Accumulation of cadmium, lead and nickel by fungal and wood biosorbents, Appl. Biochem., Biotechnol, vol. 53, pp. 133-142, dated 1995.

* cited by examiner

*Primary Examiner* — Irene Marx
(74) *Attorney, Agent, or Firm* — Banner & Witcoff, Ltd.

(57) ABSTRACT

This invention is referred to a new bacterial strain of *Bacillus* sp., to be applied in a metal biosorption process, which was deposited in the Agricultural Research Culture Collection (NRRL) International Depositary Authority, 1815 N. University Street, Peoria Ill. 61604, USA, having an accession number NRRL-B-30881. It is described, also, a sporulated and non-sporulated industrial inoculant of said bacterium, a method to produce said inoculant, and a process to remove metals by said bacterium.

1 Claim, 2 Drawing Sheets

BACTERIAL STRAIN FOR A METAL BIOSORPTION PROCESS

BACKGROUND OF THE INVENTION

1. Field of the Invention

This invention is referred to a new bacterial strain of *Bacillus* sp., useful to be applied in a metal biosorption process. It is described, besides, a sporulated and non-sporulated industrial inoculant of said bacterium, a method to produce said inoculant and a process to remove metals by said bacterium.

2. Background

Biosorption is understood as the uptake of heavy metals by biomass (living or nonliving) by physical-chemical mechanisms purely. In general terms, the biosorption process has been described as a non-selective mechanism that allows the removal of the following metals: Ag, Al, Au, Co, Cd, Cu, Cr, Fe, Hg, Mn, Ni, Pb, Pd, Pt, U, Th, Zn, and others (Gadd and White (1993). Microbial Treatment of Metal Pollution—A Working Biotechnology? Trends Biotechnol., 11, 353-359).

Nowadays, there is a large amount of international scientific literature about the capability of some microorganisms of concentrating metal ions by biosorption from diluted solutions, among them we can mention Castro et al. (1992), Biomasa de *Rhizopus oligosporus* como adsorbente de iones metálicos. Microbiología SEM 8, 94-105, Cotoras et al. (1992), Biosorption of metal ions by *Azotobacter vinelandii*. World Journal of Applied Microbiology and Biotechnology 8, 319-323, Cotoras et al. (1992), Sorption of metal ions by whole cells of *Bacillus* and *Micrococcus* Environmental Technology 13, 551-559, Fourest and Roux (1992), Heavy metal biosorption by fungal mycelial by-products: mechanism and influence of pH. Appl. Microbiol. Biotechnol. 37 pp. 399-403, Holan and Volesky (1995), Accumulation of cadmium, lead and nickel by fungal and wood biosorbents. Appl. Biochem. Biotechnol. 53 pp. 133-142. The research works have covered different groups of organisms, among which are: bacteria (e.g. *E. coli, Zoogloea ramigera, Bacillus subtilis, Azotobacter vinelandii*, etc.), fungi (e.g. *Rhizopus arrhizus, Aspergillus niger*), and algae (e.g. *Chlorella vulgaris, Sargassum* sp.). There are many reviews on the state of the art of the application of biosorption and its advances. Among them, are: Kratochvil D. and B. Volesky, Advances in the biosorption of heavy metals, Trends Biotechnol. 16 (1998), pp. 291-300; Volesky B. and Z. R. Holan, Biosorption of heavy metals, Biotechnol. Prog. 11 (1995), pp. 235-250; Kapoor, A. and Viraraghavan, T. (1995), Fungal Biosorption—An Alternative Treatment Option for Heavy Metal Bearing Wastewaters: A Review. Bioresource Technology, 53, 195-206 and Volesky Detoxification of metal-bearing effluents: biosorption for the next century Hydrometallurgy Volume 59, 203-216 (2001). From all of these researches it is possible to conclude that microorganisms can concentrate important amounts of metal ions. Values of biosorption from 0.3% to 35% of the microbial dry weight when using solutions with metals concentration between 10 and 100 mg/L have been described.

On the other hand, it is important to consider that a series of strains of the *Bacillus* type involved in processes of recovering of different metals have been described. An example: U.S. Pat. No. 5,005,130, which describes a method to recover silver from a refractory mineral of manganese dioxide and silver by using manganese-reducing bacterium *Bacillus polymyxa* and, particularly, *Bacillus polymyxa*, strain D-1, ATCC-55030, the method is based on solubilizing manganese, concentrating the silver. In the same direction, U.S. Pat. No. 5,422,268 introduces a process to recover plutonium from plutonium-polluted soils: manganese-reducing bacterium *Bacillus circulans* SD-1 NRRL B-21037 to release plutonium from soils by solubilization, and patent WO9214848, shows the application of manganese-reducing bacterium *Bacillus* sp. MBX 69 NRRL B-18768 to recover different metals from a mineral of manganese dioxide or polluted soils.

One of the most relevant requirements for the technological application of biosorption is the biomass retention, in order to allow the biosorbent to be kept in a reactor, so it can be reused. This has been frequently performed by immobilizing the microorganisms in a matrix. There are many examples on the application of these methodologies, such as the outstanding works by Brierley (Brierley, Production and application of a *Bacillus*-based product for use in metals biosorption. In: B. Volesky, Editor, Biosorption of Heavy Metals, CRC Press, Boca Raton, Fla. (1990), pp. 305-312; Brierley and Brierley, Immobilization of biomass for industrial application of biosorption. In: A. E. Torma, M. L. Apel and C. L. Brierley, Editors, Biohydrometallurgical Technologies, Proceedings of the International Biohydrometallurgy Symposium, The Minerals, Metals and Materials Society, Warrendale, Pa. (1993), pp. 35-44), who created an immobilized biosorbent based on a bacterium (*Bacillus subtilis*).

Volesky, et al., (1988) patented a method for gold biosorption using the biomass of brown seaweed attached by a natural or synthetic polymer (U.S. Pat. No. 4,769,223). In the 90's decade, the greatest part of the patents followed this example, protecting the production of pellets-shaped biosorbents by means of the artificial winning or immobilization of the biomass. This focus is also used by the following patents: Brierley, et al. (1990, U.S. Pat. No. 4,898,827) they use immobilized *Bacillus subtilis* with the metal attachment capacity of this bacterium, Greene, et al. (1991, U.S. Pat. No. 5,055,402) they used immobilized microalgae at high levels of temperature (300° C. to 500° C.). It is also important to mention the development of polymer beads, such as polysulfone to immobilize sorbents (Jeffers, et al., 1994, U.S. Pat. No. 5,279,745), which constitutes the base for BIO-FIX, developed by the Bureau of Mines of the United States. More recently, the following processes of preparation of biosorbents have been published: crosslinked yeasts by aldehydes (Yannai, et al. 1996, U.S. Pat. No. 5,538,645), biological materials beads immobilized by neutralized and crosslinked poli-(acid carboxylics) adhesive (Summers, Jr., et al. 1997, U.S. Pat. No. 5,602,071), brown seaweed which alginate has been extracted (Pohl 1997 U.S. Pat. No. 5,648,313), fungal biomass (of the types of *Aspergillus, Penicillium* y *Trichoderma*) or bacterial (*Micrococcus*) treated with phosphoric acid, solvents and sodium hydroxide (Kogtev, et al. 1998, U.S. Pat. No. 5,789,204), microorganisms immobilized in hydrophilic polyurethane (Hermann 1999, U.S. Pat. No. 5,976,847). More recently, Nakao and Suzuky (2004) introduced a metals-adsorbent composition containing *Bacillus* sp. KRI-02, *Bacillus licheniformis*, and *Staphylococcus* sp. KRI-04 bacterial cells, which is obtained by acid treatment of the bacteria (CA Patent 2497264).

Although these biosorbent materials are promising, they present the disadvantages of requiring a biomass concentration stage, usually by centrifugation, and the need of employing chemical agents that allow its immobilization as granulated or agglomerated products. Both are very expensive processes that demand a high energetic cost and employ toxic chemical products or environmental contaminants.

As an alternative, CL Patent 40704 (Cotoras and Viedma, 2000) and the patent application N° 1945-2005 (Cotoras et al., 2005) describes a process in which, first of all, a biofilm is formed spontaneously on a low-priced-inert-support material. Once the immobilization is finished, the alternated cycles of biosorption and desorption start. Nevertheless, the available microorganisms in the state of the art (e.g. *Pseudomonas, Klebsiella, Bacillus*, etc.) show a series of disadvantages to achieve an efficient performance of this process. The main difficulties are: the inoculant must be produced and transported to the decontamination plant. This is limited by the low stability of the inoculant culture and the enormous volume required. In addition, the available strains existing nowadays have a low biofilm formation and contaminants removal capacity.

This invention presents a series of alternatives to the disadvantages of the technologies available in the state of the technique, because by isolating a bacteria strain that shows a high attaching capacity it is possible to form aggregates of vegetative cells or spores and form biofilms on a solid support material. The cell aggregates generation allows producing, in a simple way, a concentrated inoculant of bacterial cells, both vegetative and sporulated. On the other hand, the high biofilm formation capacity facilitates the colonization of the inert support material, increasing the contaminants removal capacity of the biosorption process.

DETAILED DESCRIPTION OF THE INVENTION

The main object of this invention is an isolated bacterial strain of *Bacillus* sp. VCHB-10, accession number NRRL-B-30881, or a mutant, or a recombinant derived from this one.

In an embodiment of the invention, said strain shows a high attaching capacity, which allows to form aggregates of vegetative cells or spores and biofilms on a solid support material.

In another embodiment of the invention, said strain shows the capacity of removing metal ions by biosorption.

The second main object of this invention is an inoculant to be employed in the metals removal based on the isolated strain, which comprises a preparation of vegetative cells or a spores preparation of *Bacillus* sp. VCHB-10, accession number NRRL-B-30881.

In an embodiment of the invention, the inoculant comprises a preparation of vegetative cells presented as a concentrated suspension.

In a preferred embodiment of the invention, the preparation of vegetative cells is immobilized by means of supports based on polysaccharides, such as alginate, chitosan, agar or other immobilizing agents.

In another preferred embodiment of the invention, the preparation of vegetative cells is adsorbed on an inert material, such as soil, peat or sand.

In an additional preferred embodiment of the invention, the preparation is encapsulated (granulated) with an external capsule constituted by a polymer, such as coagulated alginate or other similar materials.

In a particular embodiment, the preparation of vegetative cells contains also one or more accepted excipients, such as stabilizings, osmoprotectants or inhibitors, which allow the stabilization of said inoculum.

In an embodiment of the invention, the preparation of spores is a concentrated liquid suspension.

In another preferred embodiment of the invention, the preparation of spores is dehydrated by heat drying, vacuum drying or lyophilization.

In an additional preferred embodiment of the invention, the preparation of spores is a frozen concentrated suspension.

In another preferred embodiment of the invention, the preparation of spores is immobilized by means of supports based on polysaccharides, such as alginate, chitosan, agar or other immobilizing agents.

In other preferred embodiment of the invention, the preparation of spores is adsorbed on an inert material, such as soil, peat or sand.

In other preferred embodiment of the invention, the preparation of spores is encapsulated (granulated) with an external capsule constituted by a polymer, such as coagulated alginate or other similar materials.

In a particular embodiment of this invention, the preparation of spores contains also one or more accepted excipients, such as stabilizings, osmoprotectants or inhibitors, which allow the stabilization of said inoculum.

The third main object of this invention is a method to prepare a concentrated vegetative cells or concentrated spores inoculant of isolated strain of *Bacillus* sp. VCHB-10, accession number NRRL-B-30881.

In a particular embodiment of this invention, the method to prepare a concentrated vegetative cells inoculant of isolated strain of *Bacillus* sp. VCHB-10, accession number NRRL-B-30881, comprised the stages of:
a) Inoculating the isolated strain of *Bacillus* sp. VCHB-10 in a liquid culture medium,
b) Incubating the culture under conditions that permit the formation of aggregates of vegetative cells,
c) Concentrating by sedimentation the aggregated vegetative cells from the culture,
d) Washing the aggregated vegetative cells with water or a proper aqueous solution,
e) Concentrating by sedimentation the washed aggregated vegetative cells to obtain the inoculant, and
f) Storing the inoculant obtained in the presence of accepted excipients. According to the desired inoculant, it can be obtained in fresh, dehydrated, adsorbed, encapsulated or immobilized.

In other particular embodiment of this invention, the method to prepare an inoculant of concentrated spores of isolated strain of *Bacillus* sp. VCHB-10, accession number NRRL-B-30881, comprises the stages of:
a) Inoculating the isolated strain of *Bacillus* sp. VCHB-10 in a liquid culture medium,
b) Incubating the culture under conditions that permit the formation of spore aggregates,
c) Concentrating by sedimentation the aggregated spores from the culture,
d) Washing the aggregated spores with water or a proper aqueous solution,
e) Concentrating by sedimentation the washed aggregated spores to obtain the inoculant, and
f) Storing the inoculant obtained in the presence of accepted excipients. According to the desired inoculant, it can be obtained in fresh, dehydrated, adsorbed, encapsulated or immobilized.

The fourth main object of this invention is a process for the metals biosorption from aqueous effluents by using the isolated strain of *Bacillus* sp. VCHB-10, by forming biofilms on support materials, or by forming aggregates of vegetative cells.

In a particular embodiment of this invention, the process for the metals biosorption from aqueous effluents using the isolated strain of *Bacillus* sp. VCHB-10, by forming biofilms on support materials, comprises, at least, the stages of:
a) Growing the bacterium forming a biofilm on the support material of a bioreactor,
b) Removing the culture medium from the bioreactor,
c) Letting the water containing metal ions pass into the bioreactor to remove the metal ions by means of the bacterial biofilm, until its biosorption capacity stars to diminish because of saturation, d) Eluting the metal ions uptaken by the bacterial biofilm by adding an acid, and
e) Repeating the process from stage c.

In another particular embodiment of this invention, the process for the metals biosorption from aqueous effluents using the isolated strain of *Bacillus* sp. VCHB-10, by forming cell aggregates, comprises, at least, the stages of:
a) Growing the bacterium by forming aggregates of vegetative cells in a bioreactor,
b) Sedimenting the aggregates of vegetative cells and taking away the culture medium from the bioreactor,
c) Contacting the water containing metal ions with the aggregates of vegetative cells in the bioreactor to remove them by biosorption, sedimenting the aggregates of vegetative cells, taking away the treated water, contacting again the water containing metal ions with the aggregates of vegetative cells as many times as necessary, until its biosorption capacity stars to diminish because of saturation,
d) Sedimenting the aggregates of vegetative cells and taking away the remainder water from the bioreactor,
e) Adding an acid to elute the metal ions uptaken by the aggregates of vegetative cells, and
f) Repeating the process from stage c.

The fifth main object of this invention is a process for the metals biosorption in soils by using the isolated strain of *Bacillus* sp. VCHB-10, which comprises, at least, the stage of adding to said soil a biologically pure culture of strain of *Bacillus* sp. VCHB-10, accession number NRRL-B-30881.

In an embodiment of this invention, the isolated strain of *Bacillus* sp. VCHB-10 was a Gram positive rod-shaped bacterium, sporulated and mobile during the exponential growing phase.

In another embodiment of the invention, the bacterium presents the following physiological features, determined in cultures performed at 28° C. and 37° C.:

| Morphological or Biochemical Test | Reaction at 28° C. | Reaction at 37° C. |
|---|---|---|
| Beta-galactosidase | (−) | (−) |
| Arginine dihydrolease | (+) | (+) |
| Lysine decarboxilase | (−) | (−) |
| Ornithine decarboxylase | (−) | (−) |
| Simmons citrate | (−) | (−) |
| $H_2S$ Production | (−) | (−) |
| Urease | (−) | (−) |
| Tryptophan deaminase | (−) | (−) |
| Indol production | (−) | (−) |
| Production of acetoine (Voges-Proskauer) | (−) | (−) |
| Gelatinase | (+) | (+) |
| Glucose fermentation/oxidation | Ferm (+) Oxid (+) | Oxid (+) Ferm (+) |
| Mannitol fermentation/oxidation | (−) | (−) |
| Inositol fermentation/oxidation | (−) | (−) |
| Sorbitol fermentation/oxidation | (−) | (−) |
| Rhamnose fermentation/oxidation | (−) | (−) |
| Sucrose fermentation/oxidation | Ferm (−) Oxid (+) | Ferm (−) Oxid (+) |
| Melibiose fermentation/oxidation | (−) | (−) |
| Amygdalin fermentation/oxidation | Ferm (−) Oxid (+) | Ferm (−) Oxid (+) |
| Arabinose fermentation/oxidation | (−) | (−) |
| Oxidase | (−) | (−) |
| $NO_2^-$ Production | (−) | (+) |
| $N_2$ Production | (−) | (−) |
| Glucose Oxidation | (+) | (+) |
| Glucose Fermentation | (+) | (+) |
| Others: | | |
| Gram stain | Rod (+) | Rod (+) |
| Sporulation | (+) | (+) |

(−) = Negative
(+) = Positive
Ferm = Fermentation
Oxid = Oxidation

A sample containing *Bacillus* sp. VCHB-10 strain was deposited under the provisions of the Budapest Treaty on Oct. 28, 2005, in the international collection Agricultural Research Service Culture Collection NRRL, National Center for Agricultural Utilization Research Agricultural Research Service, USDA 1815 North University Street Peoria, Ill. 61604-3999 U.S.A., and was assigned accession number NRRL-B-30881.

DESCRIPTION OF THE DRAWINGS

In FIG. 1A, it is possible to observe the biosorption stage, in which the copper-concentration of the inletting solution is represented by a dotted line, and the concentration of the treated solution is illustrated by the filled diamonds curve.
In FIG. 1B, desorption stage is shown by the empty triangle curve.

FIG. 2A illustrates de biosorption stage, in which the copper concentration of the inletting solution is represented by a dotted line and the concentration of the treated solution corresponds to the filled diamonds curve.
In FIG. 2B, desorption stage is shown by the empty triangle curve.

Figure 1:
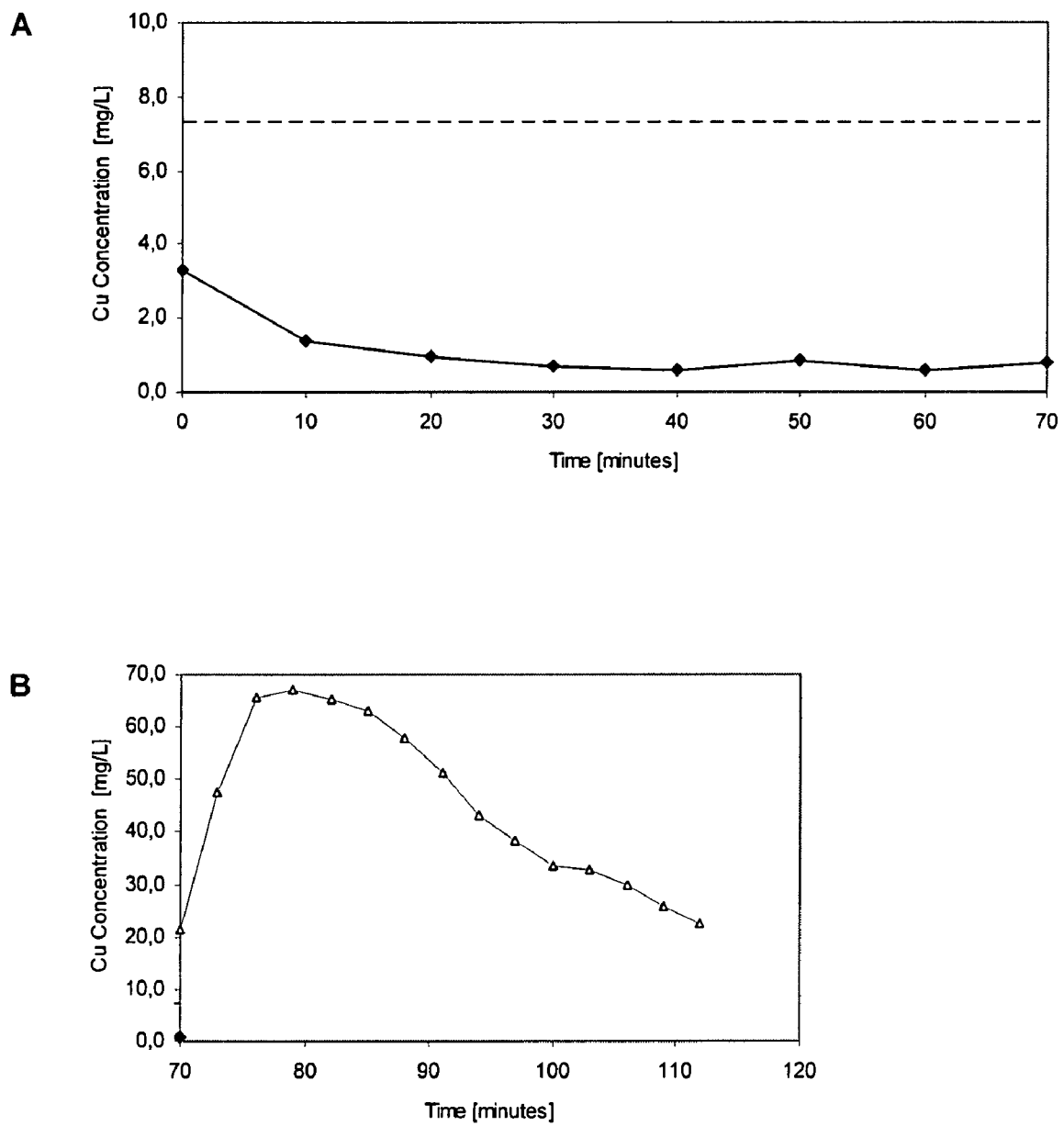
FIG. 1:
This Figure shows the curve of copper adsorption-desorption by a biofilm of strain of *Bacillus* sp. NRRL-B-30881 in a fixed bed bioreactor filled with gravel.

The following examples illustrate some concrete applications of this invention, but are not meant to limit the framework or the scope of the present invention.

EXAMPLES

Example 1

Preparation of Aggregated Vegetative Cells of Strain of *Bacillus* Sp. NRRL-B-30881 in Erlenmeyer Flasks In nine 250 mL Erlenmeyer flasks, 90 mL of culture medium N° 1 (indicated in Table 1) were prepared. These flasks were sterilized in autoclave at 121° C. for 15 minutes. Separately, 10 mL of different glucose solutions (1, 2, 3, 4, 5, 6, 8, and 10% w/v) were prepared. They were sterilized in autoclave at 121° C. for 15 minutes. Then, when cold, glucose was added to the Erlenmeyer flasks, which contain the culture medium N° 1 (from which the following final concentrations of glucose were obtained: 0, 1, 2, 3, 4, 5, 6, 8 y 10 g/L). Later, the different flasks were inoculated with strain of *Bacillus* sp. NRRL-B-30881, which was kept in slant agar tubes in a tryptic soy agar solid medium, and then was grown in an orbital stirrer at 28° C. and 150 rpm for 24 hours.

TABLE 1

Composition of culture medium N° 1 for strain of *Bacillus* sp. NRRL-B-30881

| Component | Concentration |
|---|---|
| $Na_2HPO_4 \cdot 2H_2O$ | 1.393 g/L |
| $KH_2PO_4$ | 0.333 g/L |
| $K_2SO_4$ | 0.111 g/L |
| NaCl | 0.111 g/L |
| $MgSO_4 \cdot 7H_2O$ | 0.022 g/L |
| $CaCl_2 \cdot 2H_2O$ | 0.0147 g/L |
| $FeSO_4 \cdot 7H_2O$ | 0.00203 g/L |
| Yeast extract | 1.1 g/L |
| Tryptone | 1.1 g/L |

By using a volumetric pipette, a 10 mL sample was taken from the flasks containing culture already grown and was put in a centrifuge tube. In order to determine the aggregation of the culture, the sample was settled for 10 minutes. Then, 5 mL were passed from the superior part of the tube to another centrifuge tube. Each aliquot was centrifuged at 8000 r.p.m. for 10 minutes (Centrifuge Sorwall® RC5B, Newton Conn., USA), supernatant was eliminated and the pellet was exposed to 105° C. for 48 h. The percentage of aggregation was calculated according to the formula below:

$$\% A = \frac{(P - S) \times 100}{(P + S)}$$

In this formula, % A is the percentage of aggregation; P and S are the dry weight obtained from the inferior and superior section of the tube. In order to calculate the total dry weight of the bacterial biomass, both dry weights were added (P+S).

Table 2 shows the results obtained by carrying out the cultures at different glucose concentrations. There was no remaining glucose when initial concentration was 3 g/L; however, it increases from an initial glucose concentration of 4 g/L. Final biomass, as well as cell aggregation, reaches its maximum only from a 3 g/L glucose concentration. According to this example, when the strain of *Bacillus* sp. NRRL-B-30881 was grown under proper conditions, a high percentage of aggregated biomass was obtained, which gets sedimented in 10 minutes (about a 70% of total biomass).

Sedimented biomass may be employed as a concentrated inoculant to begin a decontamination process or to be employed directly in a process of metals biosorption from aqueous effluents, by using aggregates of vegetative cells of isolated strain of *Bacillus* sp. NRRL-B-30881 as a biosorbent agent.

TABLE 2

Preparation of cell aggregates of strain of *Bacillus* sp. NRRL-B-30881 inoculant in flasks with culture medium containing different glucose concentrations.

| Initial Concentration of Glucose (g/L) | Final Concentration of Glucose (g/L) | Biomass Obtained (g dry biomass/L) | Cell Aggregation (% A) |
|---|---|---|---|
| 0 | 0 | 0.47 | 2.1% |
| 1 | 0 | 1.03 | 0.97% |
| 2 | 0 | 1.43 | 44% |
| 3 | 0 | 1.96 | 73% |
| 4 | 0.71 | 2.05 | 76% |
| 5 | 1.35 | 2.04 | 69% |
| 6 | 2.66 | 1.92 | 80% |
| 8 | 4.23 | 2.00 | 67% |
| 10 | 5.22 | 2.14 | 71% |

Example 2

Preparation of a Sporulated Inoculant of Strain of *Bacillus* Sp. NRRL-B-30881 in a 20 L Bioreactor A 20 L bioreactor (Braun Biotech International model Biostat ED, Germany) provided of a digital control system (DCU) was employed to prepare a sporulated inoculant strain of *Bacillus* sp. NRRL-B-30881. This bioreactor provides an automatic performance (acquiring information, sensors calibrating, sequential control). To measure temperature, pH, and dissolved oxygen in the culture, a probe of temperature and electrodes of pH and oxygen were employed. Inside, the bioreactor was made of stainless steel and its tank has a volume of 20 L. The capacity for culture was 15 L. The tank has a jacketed heat exchanger, four baffles, and three six-bladed flat disc impellers of 8.5 cm diameter.

Bioreactor inoculation was performed from a culture of strain of *Bacillus* sp. NRRL-B-30881 (pre-culture) in 100 mL of culture medium N° 2 (Table 3).

TABLE 3

Composition of the culture medium N° 2 for strain of *Bacillus* sp. NRRL-B-30881

| Component | Concentration |
|---|---|
| $Na_2HPO_4 \cdot 2H_2O$ | 1.254 g/L |
| $KH_2PO_4$ | 0.3 g/L |
| $K_2SO_4$ | 0.1 g/L |
| NaCl | 0.1 g/L |
| $MgSO_4 \cdot 7H_2O$ | 0.02 g/L |
| $CaCl_2 \cdot 2H_2O$ | 0.01325 g/L |
| $FeSO_4 \cdot 7H_2O$ | 0.00183 g/L |
| Yeast Extract | 1.0 g/L |
| Tryptone | 1.0 g/L |
| Glucose | 10.0 g/L |

The same medium N° 2 (Table 3) was employed for the culture in the bioreactor. The components $CaCl_2$ and glucose were sterilized in autoclave, separately. The culture was performed at 28° C. with a variable aeration, detailed farther on, with no control of pH. The samples collected were subjected to analysis of biomass, flocculation and remaining sugar. In order to measure the remaining glucose concentration, the glucose liquicolor method was employed (Human, Germany), which consists of an enzymatic-colorimetric test, which allows to measure glucose concentrations by spectrophotometry. Biomass was determined by measuring dry weight at 105° C. for 48 h. In order to obtain the percentage of aggregation, the method in example 1 was applied. Sporulation was observed by microscopy, by using spores stain on the basis of malachite green.

The culture of strain of *Bacillus* sp. NRRL-B-30881 was carried out at 120 rpm agitation speed, and a 5 L/min initial aeration, which was gradually increased until 20 L/min, in order to avoid the dissolved oxygen to become a limiting factor for growing. After 13 hours of growing, a culture with the following features was obtained:

Final biomass: 2.1 g dry biomass/L
Remaining glucose: 8 g/L
Sporulation: 100%
Cell aggregation: 100%

Thus, aggregated spores that may be easily separated from the culture broth by simple sedimentation constitute the culture obtained.

Once the culture was finished, biomass was sedimented for 1 hour. Later, samples were collected in sterile flasks. One sample was frozen and another was vacuum dried at 60° C. The stored spores by this method were easily reactivated when inoculated in a fresh culture medium (culture medium N° 2, Table 3). Thus, the spores produced of strain of *Bacillus* sp. NRRL-B-30881 are an advantageous product not only for a lengthy storing, but also for an easy transport of the inoculant.

Example 3

Metals Biosorption by a Biofilm of Strain of *Bacillus* Sp. NRRL-B-30881 in a Fixed Bed Bioreactor To perform a metals biosorption by a biofilm of strain of *Bacillus* sp. NRRL-B-30881, a fixed-bed bioreactor with a 90 L-total-capacity, using polyvinyl chloride (PVC) as material, was employed. The central structure was constituted by a type 6 piping, 315 mm nominal diameter and 1.3 m longitude PVC. The lids were PVC collector lids for 315 mm tubes, which were provided of a 12.7 mm tank outlet. To provide oxygen, a Bayer type injector was employed. This injector was constituted by the injector, made of polypropylene, and an acrylic casing. In order to keep the temperature constant at 28° C. inside the bioreactor, a heat interchange system was employed; this system consisted of a coil immersed in a water bath, which was thermo-regulated by a heater HAAKE model DC3 and a solenoid valve that controlled the inlet of cooling water, which was automatically guided by a control interface OPTO22, and the software OPTOContol, suit FactoryFloor 4.0.

Two kinds of support materials were used to fill the fixed bed bioreactor: gravel (composed by silicates and with about 6 mm average particle size) and Raschel netting (65% density). The gravel presents the advantages of having a high support area for biofilm. The disadvantages are: its excessive weight, its scarce uniformity and the mechanic deterioration it suffers. Raschel netting is a fabric elaborated from high-density polyethylene bands. It shows excellent mechanic properties and a great chemical, thermal and light stability. In both cases, a proper amount of support material was employed to fill about 70 L of the fixed bed bioreactor with a total capacity of 90 L.

The biosorption process was constituted by three main stages: culture, biosorption, and desorption. In the culture stage occurs the growing of bacteria attached to a solid support. The biosorption stage consists of the metal ions removal from the polluted industrial effluent to be treated, and the desorption stage allows the adsorbed metal ions to be eluted by applying an acid solution. The biosorption and desorption stages constitute a cycle that can be repeated many times, in order to reuse the biomass attached to the support material in the bioreactor.

Culture:

Inoculation in solid medium: the strain of *Bacillus* sp. NRRL-B-30881 was inoculated in a slant tryptic soy agar. It was grown for 24 hours at 28° C. in incubator.

Preparation of the inoculum: 2 L of culture medium N° 2 (Table 3) were prepared and divided in ten 500 mL Erlenmeyer flasks with 200 mL each one. The glucose was prepared separately. Both solutions were sterilized in autoclave at 121° C. for 20 minutes.

Preparation of culture medium: A culture medium N° 2 (Table 3) was prepared, depending on the support to be used. When the support material was composed by gravel, 45 L were prepared; and when the support material was Raschel netting, 60 L of medium were prepared.

Pre-culture: The 10 flasks were inoculated from the strain previously grown in a tryptic soy agar slant (Disco, USA). Then, it was kept in culture for 20 hours at 28° C. and with 150 r.p.m agitation, in an orbital stirrer.

Column assembling: Pressure hoses of 12.7 mm were connected to the column. To recirculate the liquid, a centrifuge pump Lowara model COM350 was employed. A compressor BAR model UB-15 provided air. The column was filled with support to a height of about 65 cm.

Culture: Culture medium and pre-culture were aggregated to the column. Culture was performed at 28° C. Air recirculation flow was set in 3 L/min and the liquid flow recirculation was set in 18 L/min. The culture was performed for 20 h.

Biosorption:

Column emptying: By the recirculation hoses, the culture was totally taken from the bottom on the column. Then, two consecutive washings were performed using 100 L of water in order to eliminate the residues.

Biosorption: A Masterflex L/S 6411-18 was connected to the inferior intake of the column. The contaminated industrial effluent (synthetic or genuine) was pumped at 400 mL/min flow by a pump Masterflex 7554-20 6-600 r.p.m. with a Easy-Load 7518-10 pump head. An effluent with a low concentration of metal ions was obtained, by overflowing, through a side outlet, which was located just above the support material in the superior area of the column.

Desorption: A pH equal to 1.0 in a 50 L volume hydrochloric acid solution was led to the column filled with gravel and 100 L were led to the column filled with Raschel netting, just like in the biosorption stage.

Results:

FIGS. 1 y 2 show the copper biosorption-desorption by means of a fixed bed bioreactor containing the biofilm of strain of *Bacillus* sp. NRRL-B-30881 on the support material. In FIG. 1, was shown the biosorption of a solution de copper sulfate (with an initial concentration of copper of 7.3 mg/L) in a bioreactor which support material was constituted by gravel. Between 0 and 70 minutes (FIG. A) it was possible to observe that the treated copper solution (filled diamonds) has a lower concentration than initial solution (dotted line), attaining nearly a 90% of copper removal. From 70 minutes of treatment (FIG. 1B), biosorption stage was interrupted and desorption stage begins with a pH 1.0 hydrochloric acid solution. The eluted solution presents a high copper concentration (empty triangles), reached at maximum concentration of 67 mg/L at 69 minutes of treatment.

Figure 2:
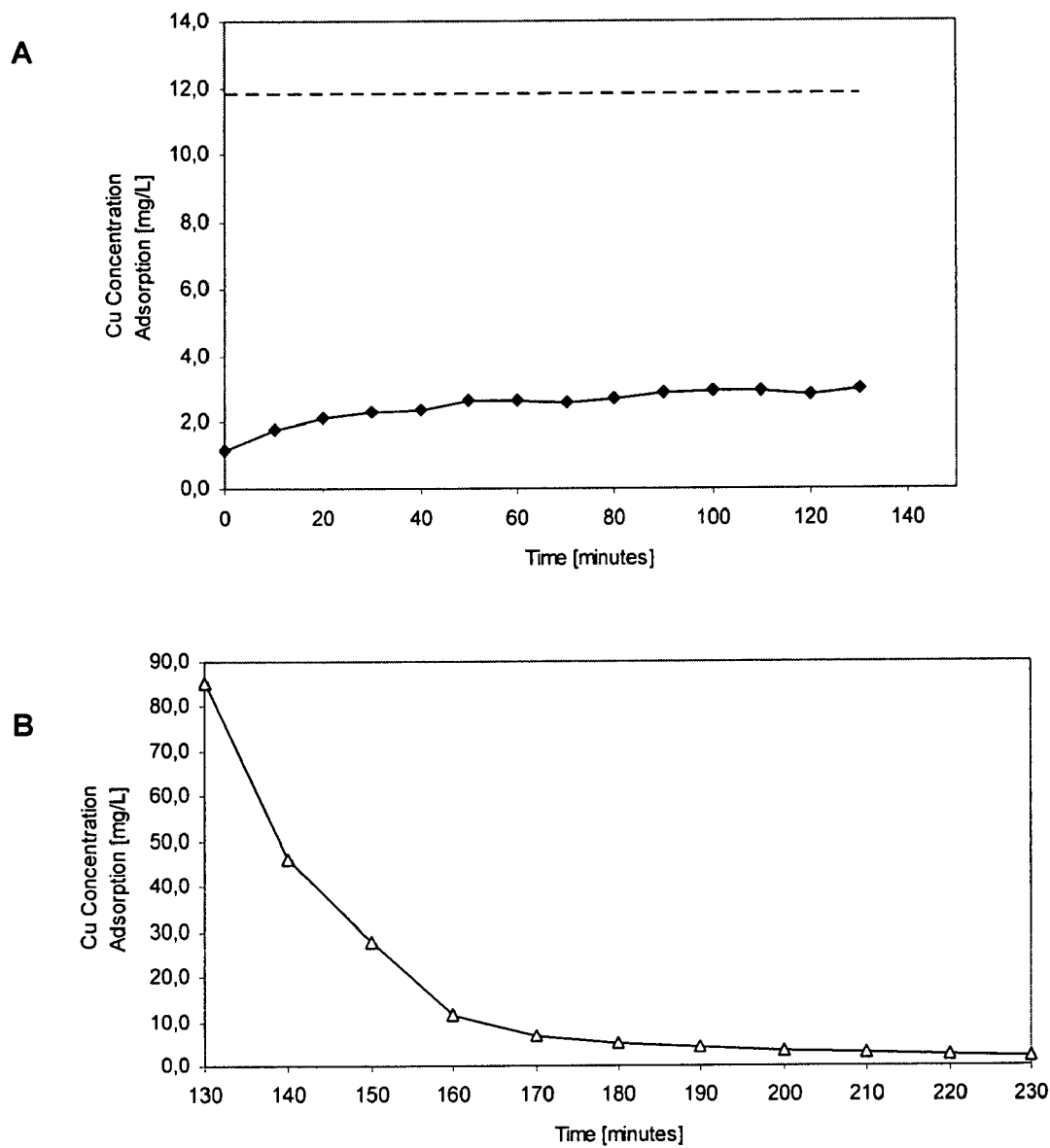
FIG. 2:
This Figure shows the curve of copper adsorption-desorption by means of a biofilm of strain of *Bacillus* sp. NRRL-B-30881 in a fixed-bed bioreactor filled with Raschel netting.

FIG. 2 corresponds to the biosorption of a copper sulfate solution (with an initial copper concentration of 11.8 mg/L) in a bioreactor filled with a column with Raschel netting, which presents a biofilm of strain of *Bacillus* sp. NRRL-B-30881. Between 0 and 130 minutes (FIG. 2A) it was possible to observe a nearly 80 and 90% of copper removal. Desorption stage occurs from 130 minutes (FIG. 2B), obtaining a highly concentrated solution (85 mg/L maximum concentration).

The invention claimed is:

1. An isolated bacterial strain of *Bacillus* VCHB-10, wherein said strain of *Bacillus* VCHB-10 has the accession number NRRL-B-30881.

* * * * *